United States Patent [19]

Sunago et al.

[11] Patent Number: 4,492,230
[45] Date of Patent: Jan. 8, 1985

[54] EXTENSION MECHANISM OF ADAPTOR FOR LASER SCALPEL

[75] Inventors: Katsuyoshi Sunago; Tomio Iwamoto, both of Osaka, Japan

[73] Assignee: Sumitomo Electric Industries, Ltd., Osaka, Japan

[21] Appl. No.: 395,309

[22] Filed: Jul. 6, 1982

[30] Foreign Application Priority Data

Jul. 7, 1981 [JP] Japan .............................. 56-100952[U]

[51] Int. Cl.³ .., ............................................ A61B 17/36
[52] U.S. Cl. ................................ 128/303.1; 128/305; 128/395
[58] Field of Search ...................... 128/303.1, 305, 395; 33/163, 164

[56] References Cited

U.S. PATENT DOCUMENTS

| | | | |
|---|---|---|---|
| 3,750,671 | 8/1973 | Hedrick | 128/305 |
| 3,865,113 | 2/1975 | Sharon et al. | 128/303.1 |
| 4,249,533 | 2/1981 | Komiya | 128/303.1 |
| 4,266,547 | 5/1981 | Komiya | 128/303.1 |

FOREIGN PATENT DOCUMENTS

| | | | |
|---|---|---|---|
| 0033958 | 8/1981 | European Pat. Off. | 128/303.1 |
| 49-94183 | 6/1974 | Japan . | |
| 51-18276 | 8/1976 | Japan . | |
| 2034961 | 6/1980 | United Kingdom . | |

Primary Examiner—Kyle L. Howell
Assistant Examiner—Christine A. Fukushima
Attorney, Agent, or Firm—Cushman, Darby & Cushman

[57] ABSTRACT

An extension mechanism of an adaptor for a laser-powered scalpel, in which an adaptor top portion is reciprocally movable in the axial direction along the length of the main body of an adaptor is disclosed. An internally threaded sleeve is mounted rotatably around the main body. The adaptor top portion includes a threaded portion engaging with the threads of the sleeve and positioned between the main body of an adaptor and the sleeve. The adaptor top portion is reciprocally movable by rotating the sleeve.

6 Claims, 4 Drawing Figures

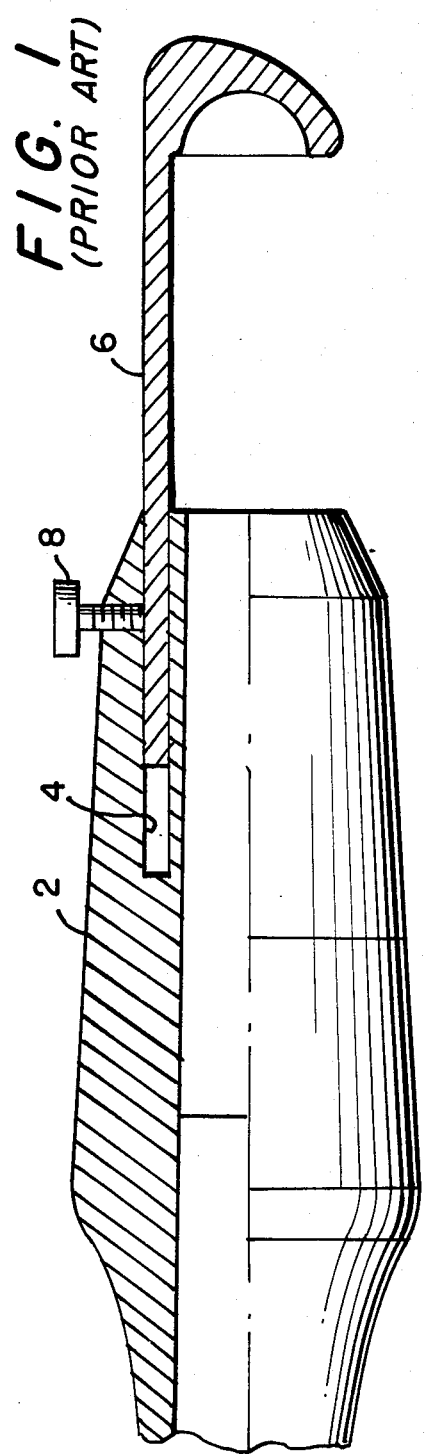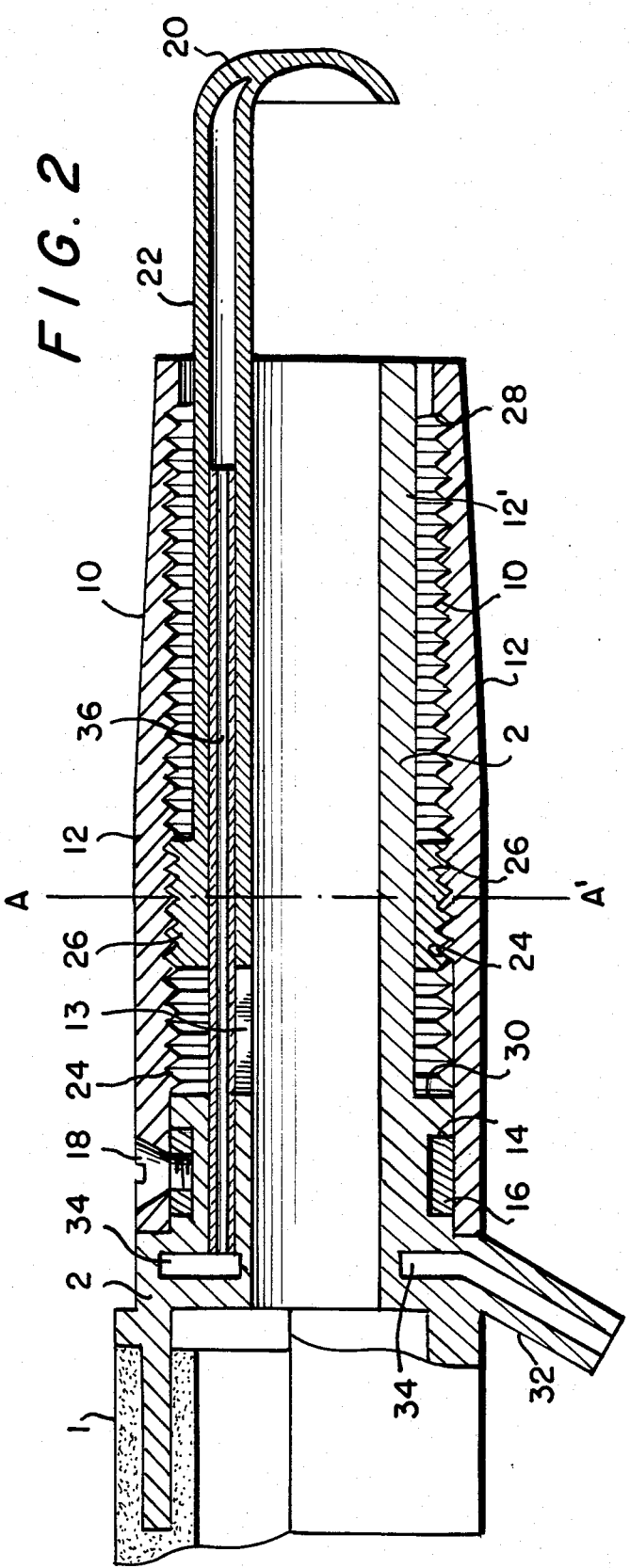

EXTENSION MECHANISM OF ADAPTOR FOR LASER SCALPEL

BACKGROUND OF THE INVENTION

This invention relates to an extension mechanism of an adaptor for a laser scalpel.

Heretofore, an extension mechanism of an adaptor for a laser scalpel has been known. As shown in FIG. 1, such mechanism includes a main body 2 provided with an axial groove 4 and an adaptor top portion 6 slidably mounted in said groove 4. The top portion 6 is fixed by means of a cap screw 8 at the desired position relative to the main body 2. The adaptor top portion 6 is so positioned that the head of the top portion is positioned under the focusing portion of the laser scalpel in order to cut the laser beam to thereby prevent further cutting of tissue under the head of the adaptor top portion 6. The depth of the tissue to be cut changes on a case by case basis. Therefore, the adaptor top must be reciprocally movable in the axial direction of the main body of the adaptor. However, this extension mechanism is defective in that it requires much time to position said top portion 6, because it requires loosening said cap screw 8 once to move said top portion 6 in and out and then screwing said cap screw 8 again thereby prolonging operation time.

SUMMARY OF THE INVENTION

An object of this invention is to provide a extension mechanism of an adaptor for a laser scalpel which can eliminate the above mentioned disadvantages of the prior art and make possible rapid positional adjustment of the adaptor top portion.

Another object of the invention is to provide an extension mechanism of an adaptor for a laser scalpel which is simple in construction and easy to operate.

The present invention may be summarized as an extension mechanism of an adaptor for a laser-powered scalpel, in which an adaptor top portion is reciprocally movable in the axial direction along the length of the main body of an adaptor. The sleeve provided with a threaded internal surface is mounted rotatably around the main body. The adaptor top portion includes a threaded portion engageable with the threads of the sleeve and positioned between the main body of the adaptor and the sleeve; the adaptor top portion is reciprocally movable by rotating the sleeve. Thereby, the position of the adaptor top portion is easily and speedily adjusted.

BRIEF DESCRIPTION OF THE DRAWINGS

FIG. 1 is a partial cross section showing the conventional extension mechanism of an adaptor, and FIG. 2 is a partial cross section showing a preferred embodiment of an extension mechanism according to the present invention.

DESCRIPTION OF THE PREFERRED EMBODIMENT

Figure 3:
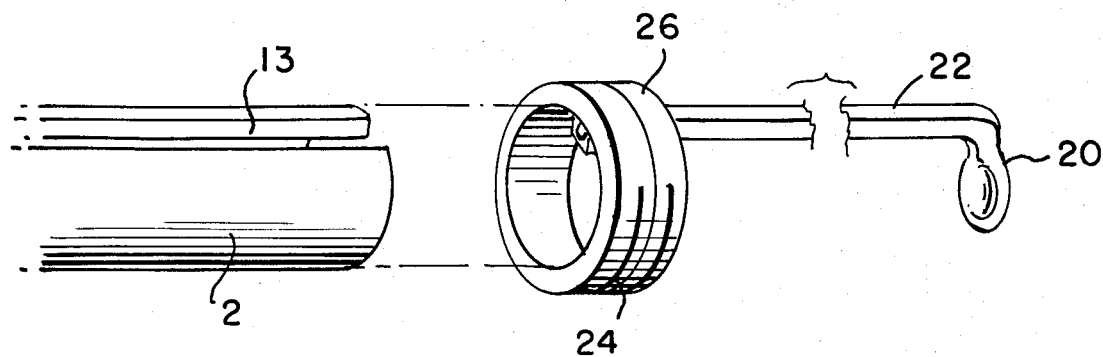
FIG. 3 is a perspective view of main body 2 and an adaptor top portion according to a preferred embodiment of the present invention prior to assembly.
Figure 4:
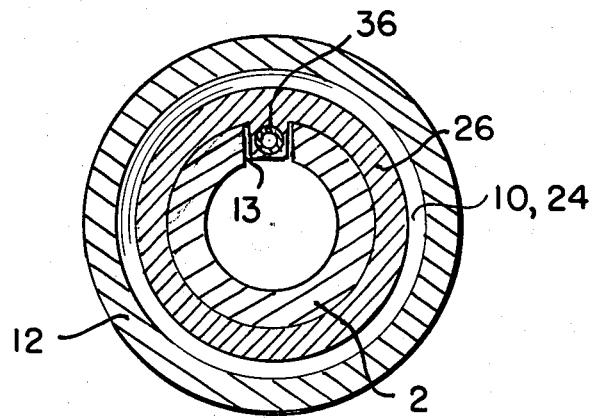
FIG. 4 is a sectional view taken along line A—A' of FIG. 2.

The preferred embodiment of the present invention will be described below by reference to FIG. 2.

FIG. 2 shows the application of the present invention to a laser scalpel provided with an adaptor for a beam receiving type of dish. The beam receiving dish cuts or interrupts the laser beam from the laser scalpel in order to prevent further cutting of tissue under the dish. Therefore, cutting of tissue is effected above the dish as is known to those skilled in the art. An adaptor holding portion 1 of the top portion of a laser scalpel is provided with a substantially cylindrical main body 2 of an adaptor. A sleeve 12 having multiple threads 10 cut on the internal surface thereof is mounted rotatably around said main body 2 of an adaptor.

Said sleeve 12 can be mounted on said main body 2 of an adaptor by, for example, forming a circumferential groove 14 in the external surface of said main body 2 of an adaptor, mounting a ring 16 in said circumferential groove 14 rotatably and connecting said sleeve 12 with said ring 16 by means of a cap screw 18. An axial guide groove 13 extending from the holding portion of the main body whereat said ring 16 to a front end is formed in a circumferential wall 12' of said main body 2 of an adaptor. An adaptor top portion, i.e. a hollow rod portion 22 of a beam receiving dish 20, is integrally provided with a ring portion 26 provided with a threaded portion 24 engaging with multiple threads 10 of said sleeve 12 at the internal end thereof. The rod portion 22 is slidably positioned in the axial guide groove 13. Said ring portion 26 is positioned between said main body 2 of the adaptor and said sleeve 12 as shown in FIG. 2. Accordingly, the rotation of said sleeve 12 leads to an axial reciprocal movement of said beam receiving dish 20, which is limited by the engagement of stopping surfaces 28 (on sleeve 12) and 30 mounted on said main body 2 of an adaptor adjacent said ring 26.

In addition, feed water, i.e. a physiological solution of sodium chloride, is introduced into said beam receiving dish 20 from a feed water pipe 32 mounted in said main body 2 of an adaptor through a feed water groove 34 mounted in said main body 2 of an adaptor, a hollow feed water needle 36 being fixed to said main body 2 of an adaptor in said guide groove 13 and said hollow rod portion 22 receiving said feed water needle 36 therein.

As described above, according to the present invention, it is necessary only to rotate said sleeve 12 in order to extend or retract said beam receiving dish 20, which forms the adaptor top portion, and thereby the position of said beam receiving dish 20 can be easily and speedily set to thereby shorten the operation time. Further, although an adaptor of beam receiving dish type is described in the above mentioned preferred embodiment, it goes without saying that an extension mechanism of an adaptor according to the present invention can be applied to adaptors of other types in which the extension of the top part of an adaptor is required.

What is claimed is:

1. An extension mechanism of an adaptor for a laser-powered scalpel, in which an adaptor holding portion of said laser scalpel is provided with a substantially cylindrical main body having a longitudinal axis, said main body supporting an adaptor top portion, said adaptor top portion being reciprocally movable in the longitudinal axial direction of said main body, wherein a sleeve provided with threads on its internal surface is mounted rotatably around said main body, said adaptor top portion including a threaded portion engaging with said threads of the sleeve and positioned between said main body and said sleeve, said adaptor top portion being reciprocally movable by rotating said sleeve.

2. An extension mechanism as defined in claim 1, wherein said adaptor top portion comprises a hollow rod having a beam receiving dish on the forward end thereof.

3. An extension mechanism as defined in claim 2, wherein said main body includes an axial guide groove in a circumferential wall of said main body and said hollow rod is slidably positioned in the guide groove.

4. An extension mechanism as defined in claim 2, wherein said main body includes a feed water groove and a hollow feed water needle fixed thereto, said needle extending into said hollow rod for feeding water to said beam receiving dish.

5. An extension mechanism as defined in claim 1, wherein said adaptor top portion includes a ring and a hollow rod integrally formed with said ring, said threaded portion of said adaptor top portion being formed on the ring.

6. An extension mechanism as defined in claim 5, wherein said main body includes stopping surfaces engageable with said ring of the adaptor top portion.

* * * * *